(12) United States Patent
Hsiao

(10) Patent No.: US 8,201,957 B2
(45) Date of Patent: Jun. 19, 2012

(54) LAMP-BASED SCENT RELEASING SYSTEM

(76) Inventor: Ming Jen Hsiao, Toufen (TW)

( * ) Notice: Subject to any disclaimer, the term of this patent is extended or adjusted under 35 U.S.C. 154(b) by 287 days.

(21) Appl. No.: 12/614,189

(22) Filed: Nov. 6, 2009

(65) Prior Publication Data

US 2011/0110092 A1  May 12, 2011

(51) Int. Cl.
*F21V 33/00* (2006.01)
*F21V 21/00* (2006.01)
*H01R 33/00* (2006.01)

(52) U.S. Cl. ............ 362/96; 362/643; 362/647; 362/391

(58) Field of Classification Search .................... 362/96, 362/101, 154, 253, 457, 549, 95, 640–659, 362/353, 391, 407; 392/393; 219/220; 439/253, 439/254, 255, 256, 257
See application file for complete search history.

(56) References Cited

U.S. PATENT DOCUMENTS

| | | | | |
|---|---|---|---|---|
| 5,097,400 A | * | 3/1992 | Cvek | 362/287 |
| 5,581,956 A | * | 12/1996 | Fennessy et al. | 52/28 |
| 5,651,942 A | * | 7/1997 | Christensen | 422/125 |
| 6,093,028 A | | 7/2000 | Yang | |
| 7,133,605 B2 | * | 11/2006 | Niemeyer | 392/390 |
| 7,309,150 B2 | * | 12/2007 | Vendrick | 362/391 |
| 2010/0270943 A1 | * | 10/2010 | Cook | 315/291 |

* cited by examiner

*Primary Examiner* — David Crowe
(74) *Attorney, Agent, or Firm* — Ming Chow; Sinorica, LLC

(57) ABSTRACT

A lamp-based scent releasing system includes a housing with light holes, a lamp holder fixedly mounted inside the housing, a lamp bulb installed in the lamp holder, a power cable connected to the lamp holder for connection to an electric outlet to obtain the necessary working voltage for the lamp bulb, a heat-transfer tray fastened to the top open of the housing and holding an aromatic substance, and a heat-resistant protective cup surrounding the lamp bulb inside the housing and having radiation holes for guiding radiation heat from the lamp bulb toward the heat-transfer tray to heat the aromatic substance to release a scent.

8 Claims, 6 Drawing Sheets

LAMP-BASED SCENT RELEASING SYSTEM

FIELD OF THE INVENTION

The present invention relates to scent releasing devices and more specifically, to a lamp-based scent releasing systems that utilizes the heat of a night lamp to heat a scented candle or aromatic substance, causing scent to be released from the scented candle or aromatic substance.

DESCRIPTION OF THE RELATED ART

A variety of night lamps are commercially available. These commercial night lamps provide different shape designs to attract consumers. However, they are commonly comprised of a lamp socket for holding a bulb, and a power input plug fixedly connected to the lamp socket at one side for connection to an electrical outlet to receive power supply. However, most conventional night lamps do not allow adjustment of the angular position of the power input plug, it is inconvenient to install a conventional night lamp in a narrow installation area.

To eliminate the aforesaid installation problem, U.S. Pat. No. 6,093,028 discloses a night lamp entitled "Night lamp with side mounting type rotary power input plug", which comprises a lamp socket holding a bulb, and a power input plug fastened to the lamp socket at one side for power input. According to this design, the power input plug comprises a body coupled to the lamp socket at one side to hold two metal blades for insertion into an electrical outlet and an annular metal contact plate and a center metal contact plate at its back side wall in connection to the metal blades respectively, and two locating blocks securely fastened to the lamp socket at one side to hold the body in place, enabling the annular metal contact plate and the center metal contact plate to be maintained in contact with a respective metal contact plate in the lamp socket. The locating blocks each have a coupling flange respectively coupled to an annular coupling groove at the periphery of the body for enabling the body to be rotated on its own axis between the locating blocks to adjust relative to the lamp socket.

Further, U.S. Pat. No. 7,133,605B2, entitled "Heater for scented candles", discloses a device for heating a scented candle so as to release scent therefrom in the absence of an open flame. The device includes a housing for retaining the candle. The housing is fabricated from a material having a low thermal conductivity. The device further includes an electrical heater in thermal communication with the housing. The heater warms the scented candle, and the low thermal conductivity housing aids in retaining heat in the candle thereby causing scent to be released therefrom.

According to U.S. Pat. No. 7,133,605B2, an electrical heater is necessary to warms the scented candle, causing the scented candle to release scent.

When a night lamp and an electrical heater for scented candles are in operation, electrical energy is been continuously consumed, costing a lot. It is a great pity that the emitted heat of the night lamp cannot be utilized while an electrical heater is in operation to provide heat for heating a scented candle to cause scent to be released from the scented candle.

SUMMARY OF THE INVENTION

The present invention has been accomplished under the circumstances in view. It is one object of the present invention to provide a lamp-based scent releasing system, which utilizes the radiation heat of a lamp bulb to heat a scented candle or aromatic substance, causing scent to be released from the scented candle or aromatic substance. It is another object of the present invention to provide a lamp-based scent releasing system, which is safe in use.

To achieve these and other objects of the present invention, a lamp-based scent releasing system comprises a housing having a top open side; a lamp holder fixedly mounted inside the housing; a lamp bulb installed in the lamp holder; a power cable connected to the lamp socket and extended out of the housing for connection to an electric outlet to obtain the necessary working voltage for the lamp bulb; and a heat-transfer tray fastened to the top open of the housing and holding an aromatic substance.

Further, the housing can be made having light holes for guiding out light from the lamp bulb, and a wire hole for the passing of the power cable.

Further, the aromatic substance can be an essential oil, a scented candle, a scented wax, or a scented dried flower.

DETAILED DESCRIPTION OF THE PREFERRED EMBODIMENT

Figure 1:
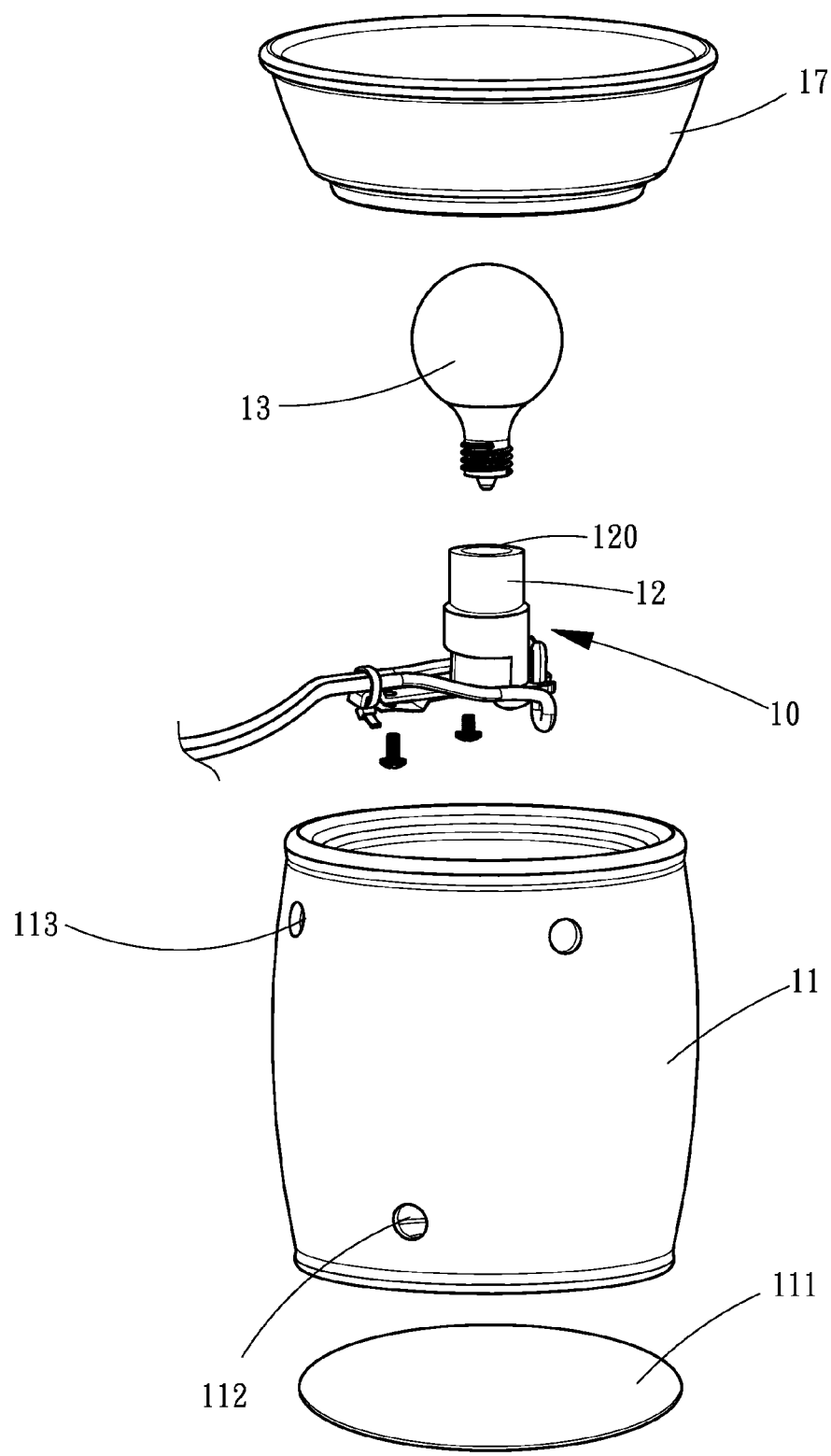
FIG. 1 is an exploded view of a lamp-based scent releasing system in accordance with the present invention.
Figure 2:
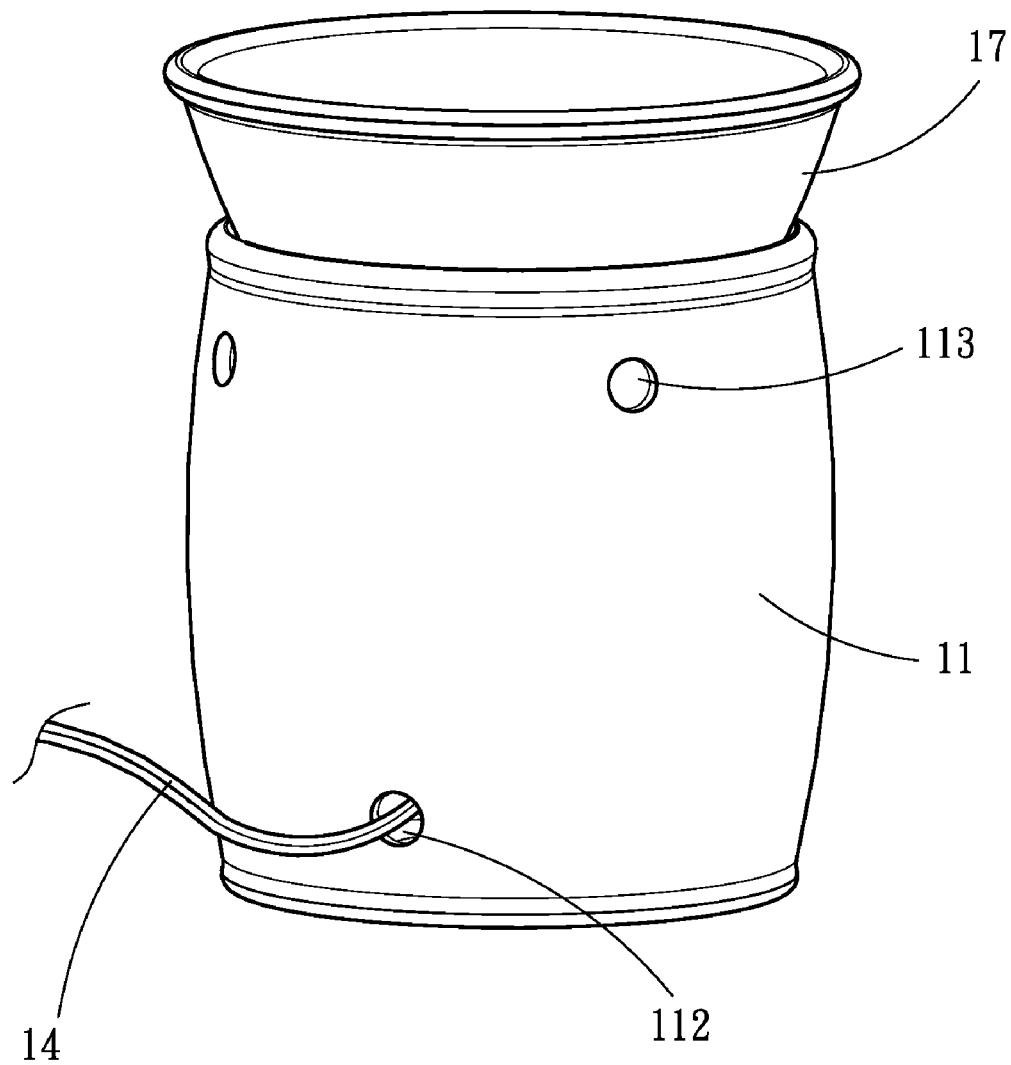
FIG. 2 is an elevational assembly view of the lamp-based scent releasing system in accordance with the present invention.
Figure 3:
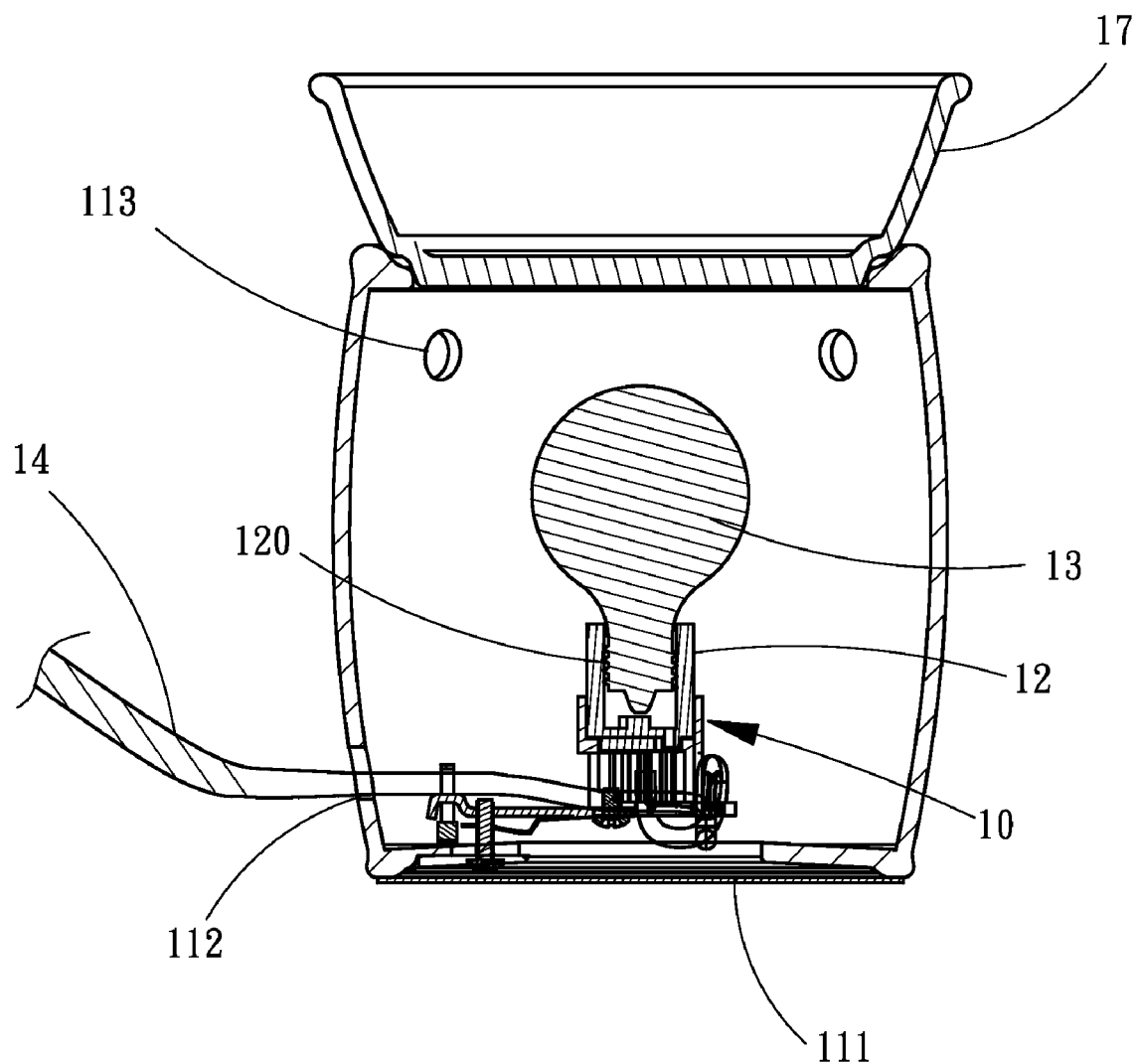
FIG. 3 is a sectional assembly view of the lamp-based scent releasing system in accordance with the present invention.
Figure 4:
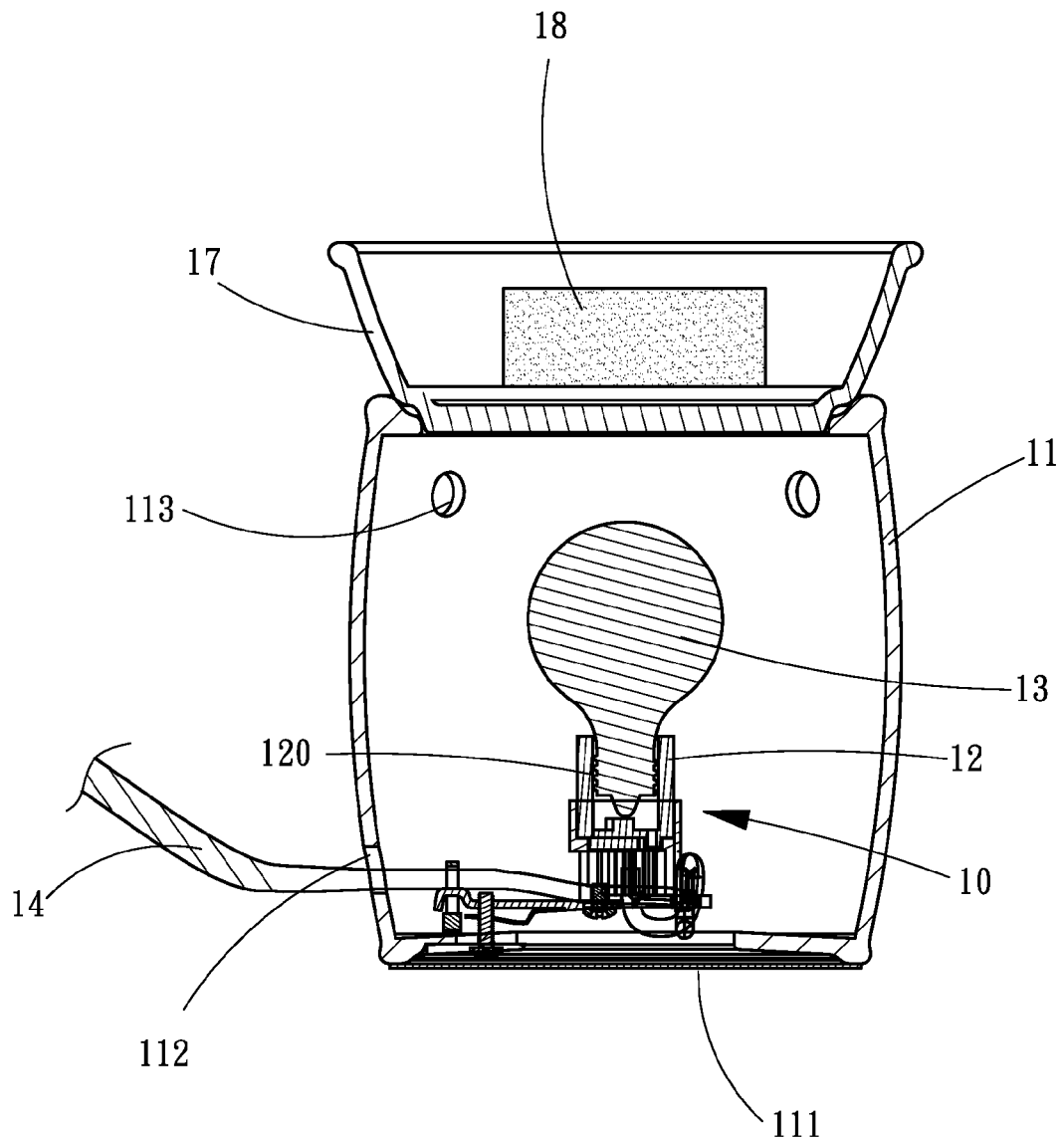
FIG. 4 is a sectional view, showing an application status of the lamp-based scent releasing system in accordance with the present invention.
Figure 5:
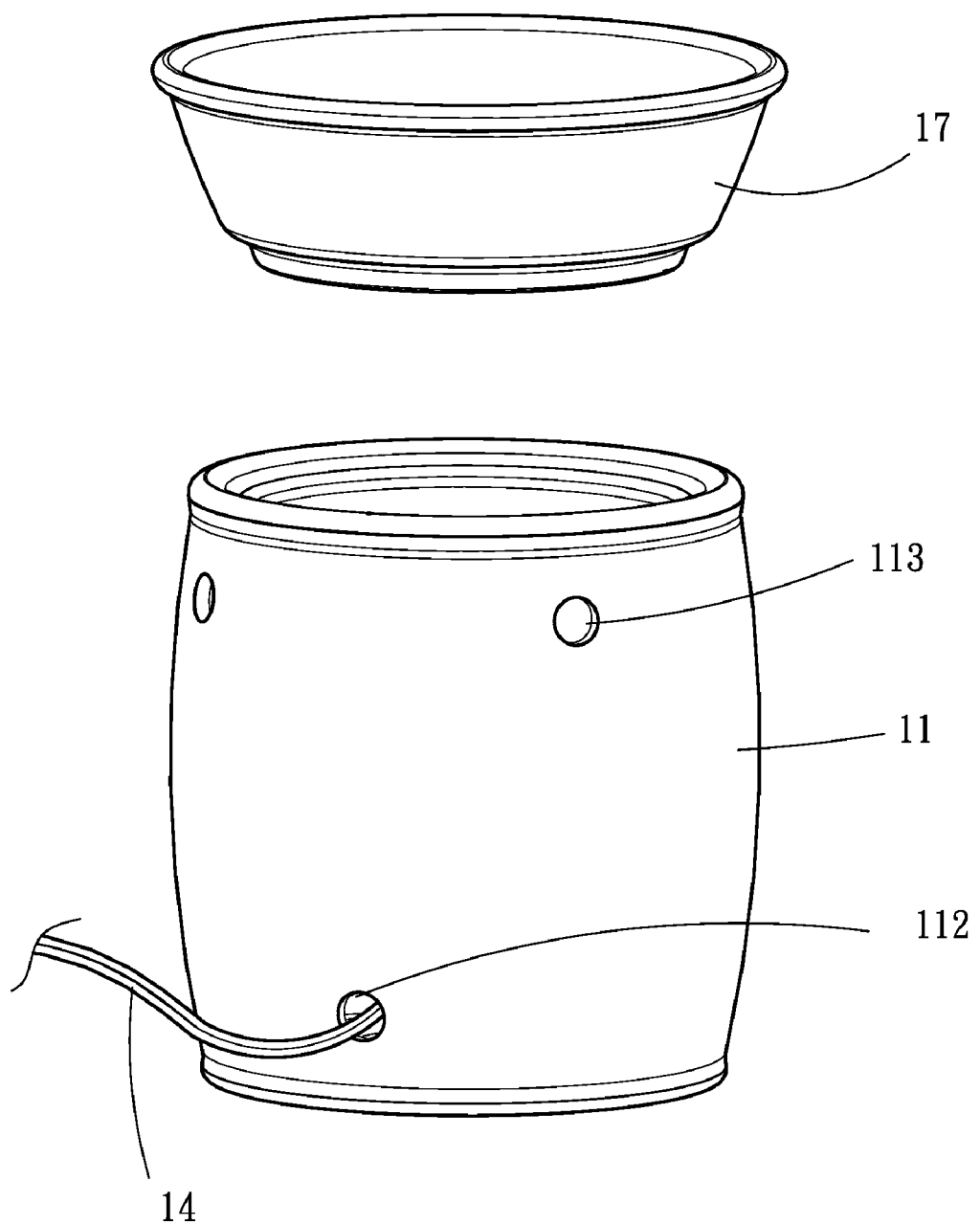
FIG. 5 is another exploded view of the lamp-based scent releasing system in accordance with the present invention.

Referring to FIGS. 1-5, a lamp-based scent releasing system in accordance with the present invention is shown comprising:

a housing 11, which is thermally conductive and light permissive hollow shell made in any of a variety of shapes, for example, the shape of a barrel, comprising a nonwoven bottom pad 111 fixedly located on the bottom side for positioning on a flat surface, for example, the top of a table, a wire hole 112 cut through the periphery near the bottom side, and a plurality of light holes 113 arranged around the periphery;

a lamp holder 10, which is mounted inside the housing 11, having an inner thread 120 (not shown), a bottom mounting frame 121, which is affixed to the bottom inside wall of the housing 11 with fastening members, for example, screws, and an outer thread 122 extending around the periphery;

a lamp bulb 13 threaded into the inner thread 120 in the lamp holder 10 and electrically connected positive-pole and negative-pole metal contacts (not shown) in the lamp holder 12 for emitting light through the light holes 113 of the housing 11;

a power cable 14 electrically connected to the lamp holder 10 and inserted through the wire hole 112 of the housing 11 to the outside for connection to an electric outlet to obtain the necessary working voltage for the lamp bulb 13;

a ceramic tray 17, which is a thermally conductive and light permissive hollow shell fastened to the top open side of the housing 11, and adapted to absorb heat energy released from the lamp bulb 13 for heating an aromatic substance 18 carried therein that can be an essential oil, scented candle, scented wax, scented dried flower, or any solid or liquid substance that release a pleasant smell when heated.

By means of connecting the power cable 14 to an electric outlet and then turning on the lamp bulb 13, the lamp bulb 13 emits light through the housing 11, providing warm illumination. At the same time, the radiation energy produced by the lamp bulb 13 falls upon the ceramic tray 17 to heat the aromatic substance 18 in the ceramic tray 17, causing the aromatic substance 18 to release a pleasant smell. Further, the housing 11 can be made capable of admitting light without the aforesaid light holes 113. Alternatively, the housing 11 can be light tight, having the aforesaid light holes 113 for the passing of light emitted by the lamp bulb 13.

It is to be understood that the housing 11 can be prepared from any of a variety of other materials, such as glass, frosted glass, acrylics, plastics, crystal, light-transmissive ceramic in a plain color or carrying a color design with/without the aforesaid light holes 113.

Further, the ceramic tray 17 is detachably connectable to the top side of the housing 11 by means of any of a variety of known connection methods such as plug joint, screw joint, friction connection or the like, facilitating cleaning and maintenance work.

Figure 6:
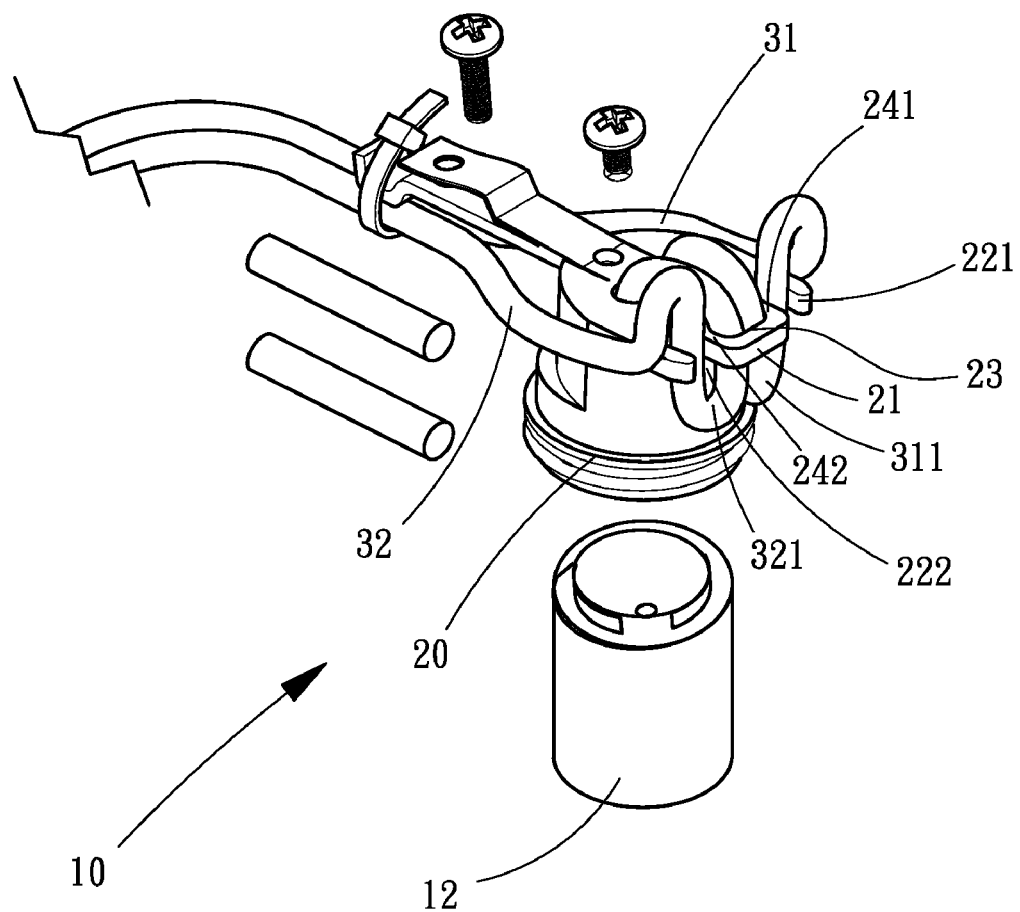
FIG. 6 illustrates the detailed structure of the lamp holder of the lamp-based scent releasing system in accordance with the present invention.

Referring to FIG. 6 and FIG. 1 again, further, the holder 10 comprises a holder base 12 prepared from ceramic and adapted for holding a lamp on the front side thereof, and a bracket 20 molded from plastics and fastened to the rear side of the holder base 12. The bracket 20 has a transversely extending extension lug 21, two wire notches 221 and 222 cut through the free end of the extension lug 21 and disposed at two opposite sides relative to the extension lug 21 and a wire hole 23 vertically cut through the extension lug 21. The extension lug 21 has two parallel arm portions 241 and 242 respectively defined between the wire notches 221 and 222 and the wire hole 23. According to the present preferred embodiment, the wire hole 23 is an oblong hole for the passing of the two insulative wires 31 and 32 of the power cable 14. The wire notches 221 and 222 have a keyway-shaped cross section, i.e., each wire notch 221 or 222 has a relatively narrower front side and a relatively larger rear side adapted for securing the insulated wires 31 and 32 of the power cable 14 positively in place.

The two insulated electric wires 31 and 32 of the power cable 14 are inserted through the wire hole 23 in direction from the rear side toward the front side and then turned outwardly apart from each other and then backwardly through the wire notches 221 and 222 respectively, each having one end respectively inserted into the inside of the holder base 12 and electrically connected to one respective metal terminal (not shown) in the holder base 12 and the other end electrically connected to one pole (the positive pole or negative pole) of power source. Thus, each insulated electric wire 31 or 32 has a U-turn portion 311 or 321 hung on the associating arm portion 241 or 242 of the extension lug 21. When the two insulated electric wires 31 and 32 of the power cable 14 are stretched accidentally by an external force, the two parallel arm portions 241 and 242 of the extension lug 21 resist against the stretching force, stopping transmission of the stretching force to the connection areas between the two insulated electric wires 31 and 32 and the two metal terminal (not shown) in the holder base 12. Therefore, the invention assures a high level of safety.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A lamp-based scent releasing system comprising:
    a housing having an open top side;
    a lamp holder fixedly mounted inside said housing;
    a lamp bulb installed in said lamp holder;
    a power cable connected to said lamp holder and extended out of said housing for connection to an electric outlet to obtain the necessary working voltage for said lamp bulb;
    a heat-transfer tray fastened to the open top of said housing and holding an aromatic substance;
    said lamp holder comprises an electrically insulative holder base adapted for holding the lamp bulb and an electrically insulative bracket molded from plastics and fastened to the rear side of said holder base;
    said electrically insulative holder base having a front side, a rear side opposite to said front side and two metal terminals fixedly mounted therein for the contact of a base contact and a ring contact of the lamp bulb;
    said bracket comprising an extension lug transversely extended from one side thereof, two wire notches cut through the free end of said extension lug and disposed at two opposite sides relative to said extension lug and a wire hole vertically cut through said extension lug;
    said extension lug having two parallel arm portions respectively defined between said wire notches and said wire hole; and
    said power cable comprises two insulated electric wires inserted through said wire hole and then turned outwardly apart from each other and then backwardly through said wire notches and respectively secured to said wire notches.

2. The lamp-based scent releasing system as claimed in claim 1, wherein said housing is prepared from ceramic that emits light.

3. The lamp-based scent releasing system as claimed in claim 1, wherein said housing comprises a wire hole for the passing of said power cable, and a plurality of light holes for guiding out light from said lamp bulb.

4. The lamp-based scent releasing system as claimed in claim 1, wherein said housing comprises a nonwoven pad fixedly provided at a bottom side thereof.

5. The lamp-based scent releasing system as claimed in claim 1, wherein said aromatic substance is an essential oil.

6. The lamp-based scent releasing system as claimed in claim 1, wherein said aromatic substance is a scented candle.

7. The lamp-based scent releasing system as claimed in claim 1, wherein said aromatic substance is a scented wax.

8. The lamp-based scent releasing system as claimed in claim 1, wherein said aromatic substance is a scented dried flower.

* * * * *